United States Patent [19]
Friedrich et al.

[11] Patent Number: 5,976,557
[45] Date of Patent: Nov. 2, 1999

[54] CARBOXAMIDOPOLYSILOXANES IN COSMETIC FORMULATIONS

[75] Inventors: Holger Friedrich, Bobenheim-Roxheim; Peter Hössel, Schifferstadt, both of Germany

[73] Assignee: BASF Aktiengesellschaft, Ludwigshafen, Germany

[21] Appl. No.: 08/972,388

[22] Filed: Nov. 18, 1997

Related U.S. Application Data

[63] Continuation of application No. 08/738,891, Oct. 28, 1996, Pat. No. 5,720,774.

[30] Foreign Application Priority Data

Nov. 19, 1996 [DE] Germany ................ 19647858

[51] Int. Cl.$^6$ ................................. A61K 7/48

[52] U.S. Cl. ................ 424/401; 424/49; 424/61; 424/62; 424/70.12; 424/70.121; 424/70.2; 424/70.6; 514/63; 514/844; 514/937; 514/943

[58] Field of Search ............... 424/401, 49, 61, 424/62, 70.12, 70.121, 70.2, 70.6; 514/63, 844, 937, 943; 556/400, 420

[56] References Cited

U.S. PATENT DOCUMENTS 5,194,251  3/1993  Halloran et al. .................. 424/70

Primary Examiner—Jyothsna Venkat
Attorney, Agent, or Firm—Keil & Weinkauf

[57] ABSTRACT

The inventions relates to carboxamidopolysiloxanes in cosmetic formulations, especially in skin-, hair-, nail- or mouth-care compositions. The cosmetic state is being improved: wet combability, combing force and static charge.

8 Claims, No Drawings

CARBOXAMIDOPOLYSILOXANES IN COSMETIC FORMULATIONS

This application is a continuation of Ser. No.08/738,891 filed Oct. 28, 1996 now U.S. Pat. No. 5,720,774.

The invention relates to the use of carboxamidopolysiloxanes of the general formula IV

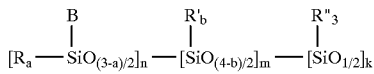

(IV)

where R, R' and R" in each case independently of one another are selected from $C_{1-6}$-alkyl or phenyl, or carboxamidpolysiloxanes of the general formula IVa

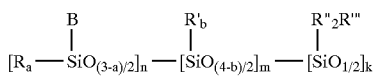

(IVa)

where R' and R" independently of one another are selected from $C_{1-6}$-alkyl or phenyl, R' and R'" independently of one another are selected from $C_{1-6}$-alkyl, $C_{1-6}$-alkoxy, OH or phenyl, and the number of types of the structural units defined by

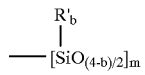

in at least 1 and a is selected from the range $0 \leq a \leq 2$ and b from the range $1 \leq b \leq 3$, and the number of repetitions of the types of structural units fixed by the variables m, n and k is selected from the ranges $1 \leq n \leq 100$ $10 \leq m \leq 800$ and $0 \leq k \leq \{(2-b)m+[(1-a)n+2]\}$, and B is an organic radical of the general formula V

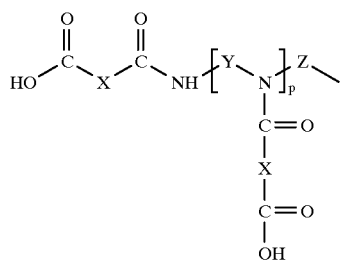

(V)

where p=0–10 and

Y and Z independently of one another are each a divalent hydrocarbon radical from the group of aliphatic hydrocarbons or a divalent alkoxyalkyl radical, and X is a divalent hydrocarbon radical from the group —$(CH_2)_y$— where $2 \leq y \leq 6$, —$CH_2$—$CHR^5$— or —$CHR^5$—$CH_2$— with $R^5$ $C_{1-20}$-alkyl or $C_{2-20}$-alkenyl, —CH=CH—, cyclic or bicyclic saturated or unsaturated hydrocarbons or the aromatic hydrocarbons.

The conditioning and caring properties of market products, especially of silicone oils, of silicone copolymers (eg. polysiloxane/polyether copolymers), of polysiloxane/polyorganobetaine copolymers, of cationically modified silicone derivatives (eg. polyquaternized polysiloxane polymers, see also DE-A 33 40 708) are inadequate and are in need of improvement. Hair and skin care products, eg, emulsions, are affected. This deficit is shown most clearly by the caring action during hair bleaching. Hair bleaching damages the hair enormously and causes a rough surface. The active ingredients known hitherto only contribute inadequately to the care and to the repair of this damaged hair.

EP-B 0 579 455 discloses oil-in-water emulsions, which contain water, a silicone oil and specific emulsifiers. These emulsions are employed in cosmetic application.

U.S. Pat. No. 5,194,251 discloses the employment of aminosiloxanes which are obtained by reaction of polydimethylsiloxanes of viscosity 10 to 15,000 cs with certain amino-containing silanes in the treatment of hair.

Silicone oils and functional siloxanes are generally used in hydrophobizing leather. Carboxyl-containing polysiloxanes are preferably used here Carboxyl-containing polysiloxanes of this type are described in DE-A 35 29 869, DE-A 38 00 629 and WO-A 95/22627. The use properties and the application results of silicone oil emulsions of this type, however, are still not optimal.

DE-A 42 14 150 discloses a process for hydrophobizing materials of fibrous structure, in which sulfosuccinic acid esters of reactive siloxanes are used.

EP-A 0 095 676 and Polymer bulletin 32, pages 175–178 (1994) disclose the conversion of aminoalkylsiloxanes into carboxamidopolysiloxanes. Carboxamidopolysiloxanes of this type are also described as carboxy-functionalized aminoalkylsiloxanes. According to EP-A 0 095 676, carboxamidopolysiloxanes of this type are used for textiles and fabric. The impart a certain softness to these materials and a certain water-repellent power. Moreover, these compounds can also be employed as mold-release agents or lubricants for metallic substrates.

In view of what has been said above, it is the object of the invention to provide cosmetic emulsions which avoid the disadvantages mentioned, in particular hair damage.

This object is achieved by use of carboxamidopolysiloxanes of the general formula IV

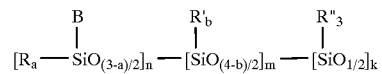

(IV)

where R, R' and R" in each case independently of one another are selected from $C_{1-6}$-alkyl or phenyl, or carboxamidpolysiloxanes of the general formula IVa

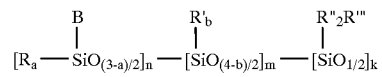

(IVa)

where R' and R" independently of one another are selected from $C_{1-6}$-alkyl or phenyl, R' and R'" independently of one another are selected from $C_{1-6}$-alkyl, $C_{1-6}$-alkoxy, OH or phenyl, and the number of types of the structural units defined by

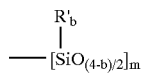

is at least 1 and a is selected from the range $0 \leq a \leq 2$ and b from the range $1 \leq b \leq 3$, and the number of repetitions of the types of structural units fixed by the variables m, n and k is selected from the ranges.

$1 \leq n \leq 100$, preferably $1 \leq n \leq 10$, $10 \leq m \leq 800$, preferably $20 \leq m \leq 150$ and $0 \leq k \leq \{(2-b)m+[(1-a)n+2]\}$, and B is an organic radical of the general formula V

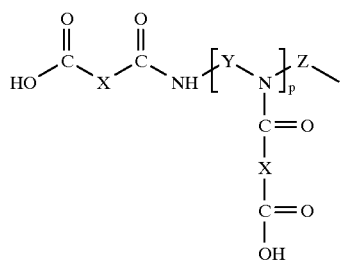

(V)

where $p = 0-10$, preferably 0 or 1 and

Y and Z independently of one another are each a divalent hydrocarbon radical from the group of aliphatic hydrocarbons or a divalent alkoxyalkyl radical, and X is a divalent hydrocarbon radical from the group $-(CH_2)_y-$ where $2 \leq y \leq 6$, preferably $2 \leq y \leq 4$, $-CH_2-CHR^5-$, $-CHR^5-CH_2-$ with $R^5$ $C_{1-20}$-alkyl or $C_{2-20}$-alkenyl, $-CH=CH-$, cyclic or bicyclic, saturated or unsaturated hydrocarbons or the aromatic hydrocarbons, in cosmetic formulations, in particular in skin, hair and nail care compositions or oral hygiene compositions.

Particularly preferred carboxamidopolysiloxanes are those of said formula IV or IVa which have a carboxyl group content from 0.02 to 2.0 mmol/g and a molar mass in the range from $1 \times 10^3$ to $60 \times 10^3$.

The object is furthermore preferably achieved by the use of the abovementioned carboxamidopolysiloxanes in which B is an organic radical of the general formula V

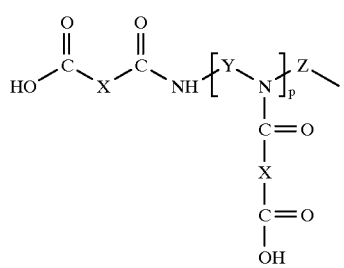

(V)

where $p = 0$ or 1, $X = -CH_2CH_2-$, $-CH_2-CHR^5-$, $-CHR^5-CH_2-$ with $R^5$ $C_{1-20}$-alkyl or $C_{2-20}$-alkenyl, preferably $C_{6-18}$-alkenyl, $-CH=CH-$ or

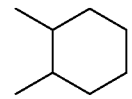
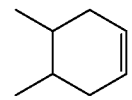
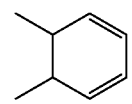
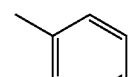
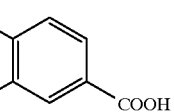

COOH $Y = -CH_2CH_2-$ and $Z = -CH_2CH_2CH_2-$.

The carboxyl-functional siloxane copolymers or carboxamidopolysiloxanes obtained for the use according to the invention by reaction of the amino-functional siloxanes of the general formula I

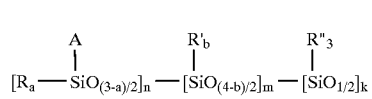

(I)

where R, R' and R" in each case independently of one another are selected from $C_{1-6}$-alkyl or phenyl, or amino-functional polysiloxanes of the formula Ia

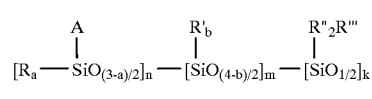

(Ia)

where R' and R" independently of one another are selected from $C_{1-6}$-alkyl or phenyl, R and R''' independently one another are selected from $C_{1-6}$-alkyl, $C_{1-6}$-alkoxy, OH or phenyl, and the number of types of the structural units defined by

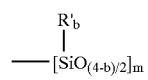

is at least 1, a being selected from the range $0 \leq a \leq 2$ and b from the range $1 \leq b \leq 3$, and the number of repetitions of the types of structural units fixed by the variables m, n and k is selected from the ranges.

$1 \leq n \leq 100$, preferably $1 \leq n \leq 10$, $10 \leq m \leq 800$, preferably $20 \leq m \leq 150$ and $0 \leq k \leq \{(2-b)m+[(1-a)n+2]\}$, and A is an organic radical of the general formula II

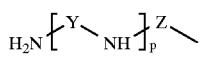
(II)

with the dicarboxylic anhydrides of the general formula III

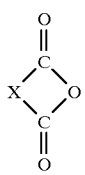
(III)

where X is a divalent hydrocarbon radical from the group —$(CH_2)_y$ where $2 \leq y \leq 6$, —$CH_2$—$CHR^5$—,—$CHR^5$—$CH_2$— with $R^5$ $C_{1-20}$-alkyl, preferably $C_{5-15}$-alkyl or $C_{2-20}$-alkenyl- preferably $C_{6-18}$-alkenyl, especially oct-2-enyl, dec-2-enyl, hexadec-2-enyl, dodec-2-enyl and octadec-2-enyl, —CH=CH—, cyclic or bicyclic saturated or unsaturated hydrocarbons or the aromatic hydrocarbons, have a structure as in formula IV shown below or the formula IVa shown above.

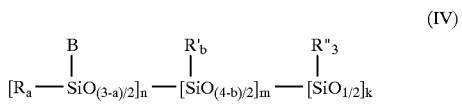
(IV)

here R, R', R", m, n, a, b and k have the meanings already mentioned, and

B is an organic radical of the general formula V given below

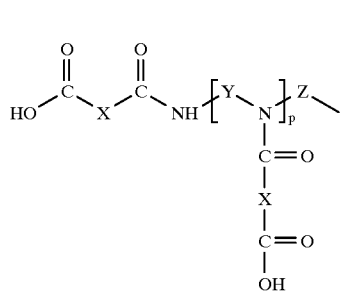
(V)

where p, X, Y and Z likewise have the abovementioned meanings.

Preferred amino-functionalized siloxanes can be prepared from the following compounds 1, 2 and 3:

A—$SiR^*_g R_{3-g}$ (1)

cyclic $(SiR'_2—O—)_n$ (2a) or linear HO—$(SiR'_2—O—)_h$H or —O—$(SiR'_2—O—)_h$ 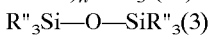 (2b)

$R"_3Si—O—SiR"_3$ (3)

with g=0–3, i.e. 0, 1, 2 or 3, preferably 0 or 3 h=3–10, preferably 3–5 and the above definitions for A, R, R' and R".

R' and R" are preferably $C_{1-3}$-alkyl, especially methyl R is preferably $C_{1-3}$-alkoxy, especially methoxy, ethoxy or OH.

The compounds are reacted under basic conditions, preferably in presence of KOH.

In the case of g=0, R=$OCH_3$, R'=$CH_3$, R"=$CH_3$ the siloxane has the following subunits:

$(CH_3)_3Si—O_{1/2}$, $(CH_3)_2Si(O_{1/2})_2$, $CH_3Si(O_{1/2})_3$, $(CH_3)_2(CH_3O)Si—O_{1/2}$, A—$Si(OCH_3)_2(O_{1/2})$, A—$Si(OCH_3)(O_{1/2})_2$, A—$Si(O_{1/2})_3$.

In the amino-functionalized siloxane thus obtained the amine number is preferably 0.1 to 0.5 meq/g. The molar ratio compound (1) to compound (2)/h is preferably 0.00375 bis 0.0375.

Instead of compound (1) the corresponding already amidized compound B—$SiR"_g R_{3-g}$ can be employed.

Compound (1) is used for functionalizing, compound (2) for forming the chains and compound (3) for terminating.

The amino-functional siloxanes employed preferentially have a viscosity in the range from 10 $mm^2/s$ to about 10000 $mm^2/s$. This corresponds to a molar mass in the range from $2 \times 10^3$ to $60 \times 10^3$ g/mol. If aminosiloxanes are employed whose viscosity is above the range mentioned, the carboxamidopoolysiloxanes obtained therefrom often have unsatisfactory properties. In particular, the products are then often inhomogeneous and/or no longer stirrable on account of too high a viscosity. If, on the other hand, the molar mass of the aminosiloxane employed falls below the range mentioned, the adherence of the carboxamidopolysiloxane prepared to the treated material, in particular hair, is poor and/or its processability is unsatisfactory. Highly preferably employed aminosiloxanes have a viscosity in the range from 50 to 500 $mm^2/s$.

The carboxamidopolysiloxanes preferably used according to the invention have a carboxyl group content from 0.02 to 2.0 mmol/g, but most preferably 0.2 to 0.5 mmol/g.

Preferably, the reaction products according to the abovementioned formula IV or IVa are employed for hydrophobization as an aqueous stable emulsion, more highly preferably as aqueous emulsions having a siloxane content of 3–90% by weight, in particular 5–60% by weight, particularly preferably 7–40% by weight.

The aqueous emulsions are prepared according to the processes described in DE-A 35 29 865, DE-A 38 00 629 and WO-A 95/22627, for example by mixing the carboxyl-functional siloxane well with water and an amine or ammonia or sodium hydroxide solution or potassium hydroxide solution (or a combination of the compounds) at 0–100° C., preferably at 20–70° C. The sequence in which the components are mixed together is immaterial here. The aqueous mixture is then processed in a suitable homogenizer (eg. gap homogenizer) to give an emulsion. Before emulsification, the oils and emulsifiers mentioned further below can additionally be added. These are preferably mixed in before homogenization.

As a further additive, it is possible to add oil or fatty acids in a concentration of 0.1–5% by weight to the emulsion.

In particular, the siloxanes of the general formulae I or Ia and IV or IVa are linear siloxanes having terminal organofunctional groups, where n =2, a=2, b=2, R=R'=R'=$CH_3$, R'"=$OCH_3$ or OH, Y =—$CH_2CH_2$—, Z=—$CH_2CH_2CH_2$— and p=0 or 1, the other substituents and variables having the meanings already mentioned. Particularly preferred among the siloxane copolymers of the general formulae I or Ia and IV or IVa are linear siloxanes having terminal trimethoxysilyl radicals and lateral organofunctional groups, where n=1–5, m=10–100, a=1, b=2, R=R'=R"=$CH_3$, R'"=$OCH_3$ or OH, Y=—$CH_2CH_2$—, Z=—$CH_2CH_2CH_2$— and p=0 or 1 and the other substituents and variables have the meanings mentioned. Most preferably, p=0. Before emulsification R'" is usually OCH$_3$, during contacting with water usually hydrolysis to OH occurs.

The siloxanes of the general formula I or Ia or IV or IVa preferably have molar masses in the range from 3000 to 10000. Linear, branched or cyclic siloxanes are suitable, it being possible for the linear or branched siloxanes to have silanol, hydrocarbon or triorganosiloxy end groups. In a preferred variant, linear or branched siloxanes are used for hydrophobization, which have end groups of the following formula VI $$[R_a-\underset{\underset{B}{|}}{SiO_{(3-a)/2}}] \qquad (VI)$$

where a=2.

Furthermore, the siloxane copolymers described in formula I or IA and IV or IVa can have various siloxy units which are characterized by different quotients of the variables a/n and/or b/m. Thus a siloxane copolymer can contain, for example, linear units.

$$[\underset{\underset{R'_b}{|}}{SiO_{(4-b)/2}}]$$

where b=2. At the same time, it has branching points where b=1 and end groups are contained where b=3.

The same applies to the given siloxane units of the following structure:

$$[R_a-\underset{\underset{B}{|}}{SiO_{(3-a)/2}}]$$

Suitable radicals R, R' or R" are preferably methyl, phenyl or ethyl radicals, and R=R'=Me is particularly preferred.

The radicals X are preferably the following divalent hydrocarbon radicals: —CH=CH— or —CH$_2$—CH$_2$—, —C(R$^1$R$^2$)—CH$_2$—, where R$^1$ or R$^2$=—(CH=CH)$_d$(CR$^3$R$^4$)$_k$—Q, where 0≦d≦2, 0≦k≦30; Q is selected from H, COOH; R$^3$ or R$^4$ is H or CH$_3$ or

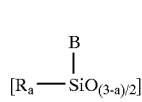

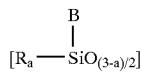

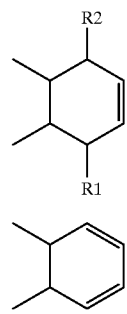

where R$^1$, R$^2$ are independent of one another and are H, C$_1$–C$_{30}$-alkyl (linear or branched), eg. methyl, ethyl, etc., or C$_2$–C$_{30}$-alkenyl (linear or branched), eg. allyl, hexenyl, dodecenyl, etc., or phenyl or substituted aryl compounds, the substituents preferably being chlorine, alkoxy or acyloxy.

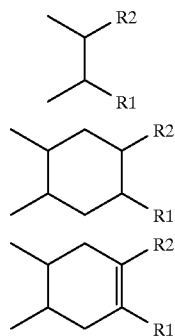

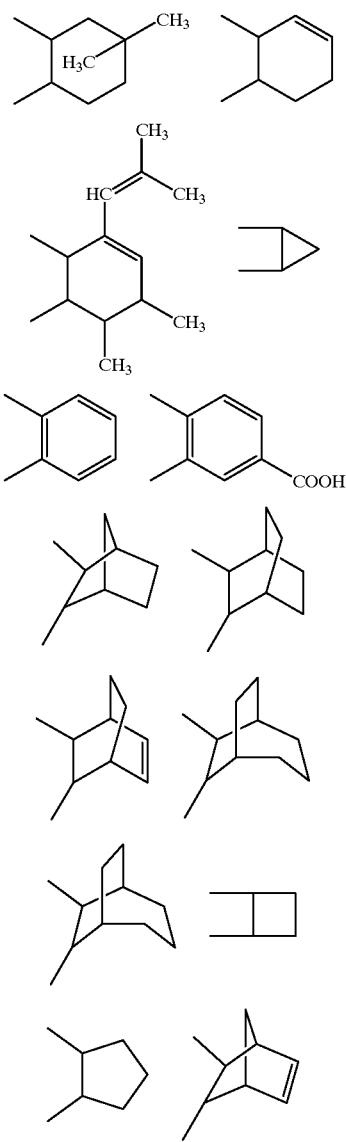

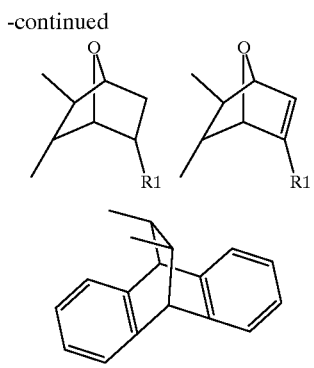

The radicals Y and Z are preferably divalent hydrocarbon radicals such as ethylene, dimethylene, hexamethylene, octaethylene and/or oxygen-containing divalent hydrocarbons such as ethylene oxide, trimethylene oxide or oligomers or polymers of these compounds. Particularly preferably Y=—CH$_2$—CH$_2$— or —CH$_2$—CHR$^5$— or —CHR$^5$—CH$_2$— with R$^5$, C$_{6-18}$-alkenyl and Z=—CH$_2$—CH$_2$—CH$_2$—. The variable p can assume values from 0 to 10, but preferably p=0 or 1. Most preferably, p=0 and Z=—CH$_2$—CH$_2$—CH$_2$—.

A preferred compound is (CH$_3$)$_3$Si—(CH$_3$)$_2$)$_n$—(O—SiBCH$_3$)$_3$)$_m$—OSi(CH$_3$)$_3$ with B=CH$_2$—CH$_2$—CH$_2$—NH—CH$_2$—CH$_2$—NH$_2$, preferably with a viscosity of approximately 200 mm$^2$/s a an amino number of 0.27. The reaction of the amino groups is preferably carried out using octyl succinic acid anhydride.

A compound (IV) is obtained:

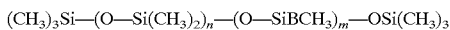

with B:

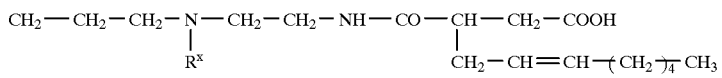

with R$^x$:

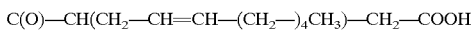

The carboxyl groups of the compounds according to formula IV or IVa can be present both as free carboxylic acids and in partial or complete salt form, for example as alkali metal salts such as sodium or potassium salts, as ammonium salts or as alkylammonium salts, 2-Amino-2-methylpropan-1-ol, ethanolamine, triethanolamine and/or morpholine are particularly preferred. In general, they are employed in their salt form.

The polysiloxane emulsions described customarily contain from 3 to 90% by weight, in particular 5 to 60% by weight, particularly preferably up to 40% by weight, of carboxyl-functionalized polysiloxanes according to formula IV. The emulsions are normally employed in amounts from 0.1 to 20% by weight, in particular 0.5 to 15% by weight.

The carboxamidopolysiloxanes are preferably used as hair setting lotions, as conditioners, as thickening agents and as auxiliaries in hair dyeing, hair bleaching and in the permanent wave process. The carboxamidopolysiloxanes are particularly advantageously employed in the form of emulsions. These emulsions can contain all active ingredients and auxiliaries customary in cosmetics.

Customarily, emulsifying substances are brought together with water, oils, fats and, if appropriate, fatty alcohols, fatty acids, preservatives, polymers, consistency imparting agents and gel-forming substances.

Active ingredients which can be contained are light screens, bleaching agents, hair-dyeing agents, permanent wave agents, cationic surfactants, anionic surfactants, humectants, urea, vitamins, panthenol, panthenol ethyl ether and/or bisabolol.

In the sues according to the invention, in addition to the carboxamidopolysiloxanes it is also possible to employ all constituents normally used in cosmetic compositions, in particular ionic and nonionic surface-active agents, foam synergists, foam stabilizers, opacifying agents, sequestering agents, thickeners, emulsifiers, plasticizing agents, preservatives, protein derivatives, natural substances, dyes, perfumes and, if appropriate, other polymers or auxiliaries.

If the polymers according to the invention are applied to the hair as aqueous, aqueous-alcoholic or alcoholic compositions or in cosmetic emulsions, then it can be disentangled more easily and has a distinctly improved wet combability than is the case when using the abovementioned silicone-containing derivatives or quaternary polyammonium polymers having hydrocarbon chains. The hair is less electrostatically charged, which facilitates hairdressing. The hair is found to be in a very good cosmetic condition, the extremely good pleasant handle of the dry hair is striking. The advantages are seen most clearly in a cosmetic emulsion (see Examples).

If the polymers according to the invention are applied to the skin as aqueous, aqueous-alcoholic or alcoholic compositions or in cosmetic emulsions, then a pleasant skin sensation can be produced. The skin sensation is better than with the abovementioned silicone-containing derivatives or with quaternary polyammonium polymers having hydrocarbon chains.

The invention is illustrated in greater detail below by Examples.

PREPARATION EXAMPLE 1

A total of 300 g of a polydimethylsiloxane having terminal aminopropyl radicals (amine number; 0.46 meq(g) is initially introduced under protective gas into a 3-necked flask which is equipped with a stirrer and internal thermometer, and the mixture is heated to 70° C. on a water bath. Succinic anhydride (13.9 g) is ground in a A10 laboratory analysis mill and slowly metered into the siloxane via a powder funnel. The mixture is subsequently stirred slowly at 70° C. for 4 hours and then cooled to 50° C.

By means of IR spectroscopy, the complete conversion of aminosiloxane and succinic anhydride into a carboxyl-functional siloxane of the structure shown below was demonstrated. (The anhydride band at about 1780 cm$^{-1}$ disappears and two new carbonyl bands, 1620 cm$^{-1}$ and 1720 cm$^{-1}$, are formed, COOH stretching vibration 2400–3500 cm$^{-1}$). Successful reaction was also demonstrated by means of $^{13}$C-NMR.

1200 g of deionized water and 8.5 g of ethanolamine are added to the reaction product described above and the mixture is emulsified at 50° C. for 10 min using an Ultraturrax (Euro Turrax T20b from IKA). This preemulsionn is then additionally processed in a gap homogenizer to give a storage-stable emulsion.

Structure of the reaction product:

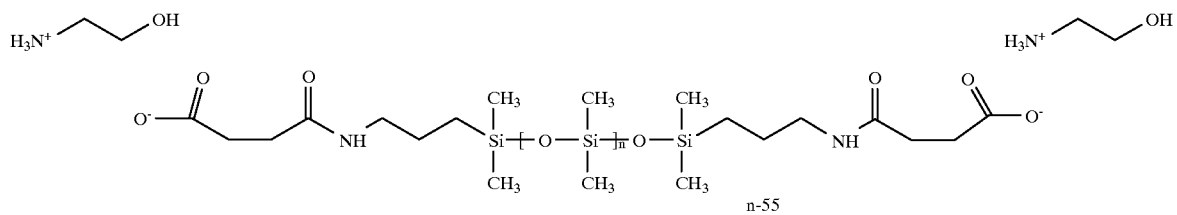

PREPARATION EXAMPLE 2

A silicone emulsion is prepared according to Example 1. Instead of ethanolamine, however, 12.4 g of 2-amino-2-methylpropanol are employed for neutralization.

Structure of the reaction product:

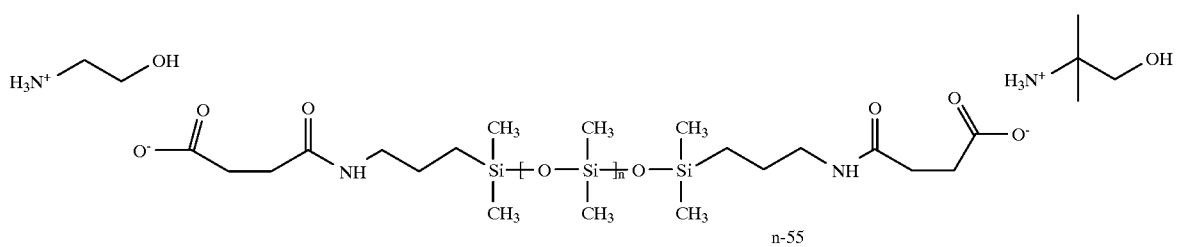

PREPARATION EXAMPLE 3

Preparation Example 2 was repeated, a pH of 6 to 6, however, being maintained.

TEST EXAMPLES

Tests:

Wet combability; subjective assessment of trained experienced hairdressing and laboratory personnel on strands of hair Marking scale: 1 (very good), 2 (good) and 3 (poor)

Double determination by two people on bleached strands of hair using middle European hair width; width 6 cm; length 25 cm Decrease in combing force; testing of the wet combability on a tensile/pressure test machine. Measurement of the decrease in combing force in comparison with an untreated strand of hair. Mean values from 15 individual measurements; hair as above.

Static charge: subjective assessment of trained experienced hairdressing and laboratory personnel after combing the abovementioned strands of hair 10 times in the dry state in an air-conditioned room at 50% relative humidity.

Marking scale: 1 (none, 2 (weak), 3 (strong)

Handle of the dry hair; subjective assessment of trained experienced hairdressing and laboratory personnel Marking scale: 1 (very soft), 2 (soft), 3 (rough)

Preparation of the test emulsions

Emulsion 1

| Phase A: | |
| --- | --- |
| 1.00 | silicone derivative (active ingredient) |
| 1.50 | ceteareth-25 |

-continued

| | |
| --- | --- |
| 1.50 | ceteareth-6 and stearyl alcohol |
| 6.00 | cetearyl octanoate |
| 3.00 | cetearyl alcohol |
| Phase B: | |
| 2.00 | propylene glycol |
| 0.30 | imidazolidinylurea |
| 0.10 | benzyl alcohol, methylchloroisothiazolinone, methylisothiazolinone |
| to 100.00 g | water |

Emulsion 2

| Phase A: | |
| --- | --- |
| 1.50 | ceteareth-25 |
| 1.50 | ceteareth-6 and stearyl alcohol |
| 6.00 | cetearyl octanoate |
| 3.00 | cetearyl alcohol |
| Phase B: | |
| 1.00 | silicone derivative (active ingredient) |
| 2.00 | propylene glycol |
| 0.30 | imidazolidinylurea |
| 0.10 | benzyl alcohol, methylchloroisothiazolinone-methylisothiazolinone |
| to 100.00 g | water |

Phases A and B were heated separately to 80° C. with stirring. Phase A was added to phase B with stirring and cooled.

The pH was adjusted by citric acid after preparation.

TABLE 1

Results of the application tests

| Polymer No. | Emulsion No. | pH | Wet combability (mark) | Decrease in combing force % | Static charge | Handle (mark) |
|---|---|---|---|---|---|---|
| Preparation Example 1 | 2 | 2–3 | 1–2 | 69 | 1 | 1–2 |
| Preparation Example 2 | 2 | 2–3 | 1 | 72 | 1 | 1 |
| Preparation Example 3 | 2 | 6–7 | 1 | 75 | 1 | 1 |
| Comparison Examples | | | | | | |
| without polymer | without polymer | 2–3 | 2–3 | 0 | 3 | 3 |
| Quaternium 80 | 1 | 2–3 | 2–3 | 25 | 3 | 3 |
| Dimethicone copolymer | 1 | 2–3 | 2–3 | 16 | 3 | 3 |
| Polyquaternium 11 | 2 | 2–3 | 2 | 36 | 3 | 2 |
| Dimethicone-propyl-PG betzine | 1 | 2–3 | 3 | 11 | 3 | 3 |
| Dimethicone-propyl-PG-bataine | 2 | 2–3 | 3 | 17 | 3 | 3 |

We claim:

1. A skin and hair composition, said composition comprising a) 1 to 90% by weight of a carboxamidopolysiloxane of the formula IV

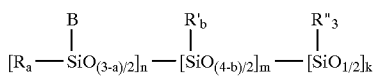   (IV)

where R, R' and R" in each case independently of one another are selected from the group consisting of $C_{1-6}$-alkyl, phenyl and a carboxamidopolysiloxane of the formula IVa

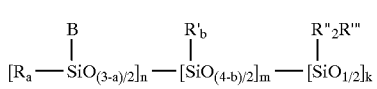   (IVa)

where R' and R" independently of one another are selected from the group consisting of $C_{1-6}$-alkyl and phenyl; R and R'" independently of one another are selected from the group consisting of $C_{1-6}$-alkyl, $C_{1-6}$-alkoxy, OH and phenyl; and the number of structural units defined by

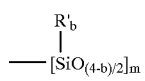

is at least 1; a having the range $0 \leq a \leq 2$; and b having the range $1 \leq b \leq 3$, and the number of repetitions of the structural units fixed by the variables m, n and K is selected from the group consisting of the ranges $1 \leq n \leq 100$, $10 \leq m \leq 800$ and $0 \leq k \leq \{(2-b)m+((1-a)n+2)\}$;

and B is an organic radical of the formula V

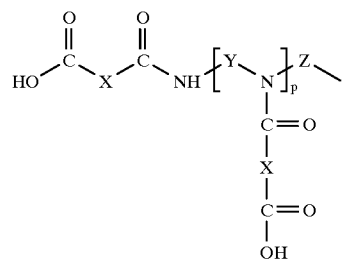   (V)

where p is 0 to 10; and

Y and Z independently of one another are each a divalent hydrocarbon radical selected from the group consisting of ethylene, dimethylene, hexamethylene, octaethylene, ethylene, oxide and trimethylene oxide, or oligomers or polymers of these radicals; and X is a vidalent hydrocarbon radical selected from the group consisting of $-(CH_2)_y-$ where $2 \leq y \leq 6$, $-CH_2-CHR^5-$, $-CHR^5-CH_2-$ (where $R^5$ is selected from the group consisting of $C_{1-20}$-alkyl and $C_{2-20}$—alkenyl), $-CH=CH-$,

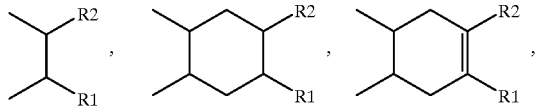

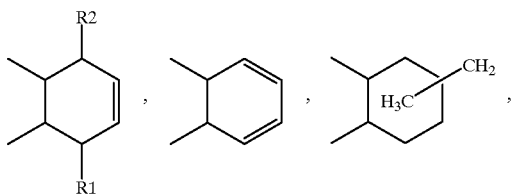

-continued

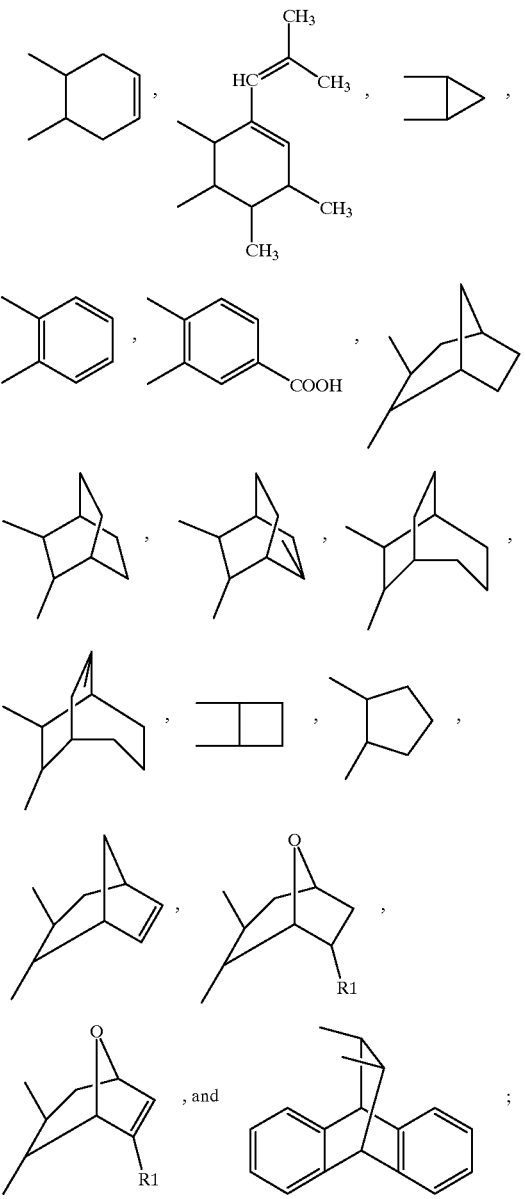

where R¹ and R², independently of one another, are selected from the group consisting of H, $C_1$–$C_{30}$-alkyl, $C_2$–$C_{30}$-alkenyl, and phenyl;

0 to 30% by weight of an emulsifier;

0 to 50% by weight of a compound selected from the group consisting of paraffin, paraffin oil, a mineral oil, a natural grease, a synthetic wax and a natural wax; and 0.1 to 5% by weight of an additive selected from the group consisting of an oil and a fatty acid; wherein water makes up the remainder of the total weight of the composition.

2. The composition defined in claim 1, wherein the carboxamidopolysiloxane of formula IV or IVa has a carboxyl group content of from 0.02 to 2.0 meq/g and a molar mass in the range of from 1000 to 60,000.

3. The composition defined in claim 1, wherein, in the radical B of formula V, p is 0 or 1;

X is selected from the group consisting of —$CH_2CH_2$—, —$CH_2$—$CHR^5$—0 and —$CHR^5$—$CH_2$—, where $R^5$ is selected from the group consisting of $C_{1-20}$-alkyl, $C_{2-20}$-alkenyl, —CH=CH—,

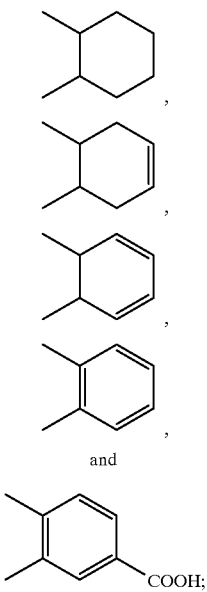

and

Y is —$CH_2CH_2$— and Z is —$CH_2CH_2CH_2$—.

4. The composition defined in claim 1, wherein the carboxamidopolysiloxane has a carboxyl group content of from 0.2 to 0.5 mmol/g and a molar mass in the range of from 30000 to 10000.

5. The composition defined in claim 1, where X is selected from the group consisting of —$CH_2$—, $CHR^5$— and —$CHR^5$—$CH_2$—, where $R^5$ is pg,30 selected from the group consisting of $C_{6-18}$-alkenyl, —CH=CH— and —$CH_2$—$CH_2$—.

6. The composition defined in claim 1, wherein the nonamidated carboxyl group of the carboxamidopolysiloxane is at least partially present in neutralized form.

7. The composition defined in claim 1 which is in the form of an emulsion.

8. The composition defined in claim 1 which is in a formulation selected from the group consisting of a shampoo, a hair setting lotion, an auxiliary for hair dyeing, a hair bleaching or the permanent wave process, oral hygiene, and a finger- and toenail care formulation.

* * * * *

UNITED STATES PATENT AND TRADEMARK OFFICE
CERTIFICATE OF CORRECTION

PATENT NO.: 5,976,557

DATED: November 2, 1999

INVENTOR(S): FRIEDRICH et al.

It is certified that error appears in the above-identified patent and that said Letters Patent is hereby corrected as shown below:

Col. 14, claim 1, line 45, "ethylene, oxide" should be --ethylene oxide--.

Col. 16, claim 4, line 41, "30000" should be --3000--.

Col. 16, claim 5, line 44, delete "pg,30".

Signed and Sealed this

Twenty-second Day of August, 2000

Attest:

Q. TODD DICKINSON

*Attesting Officer*  *Director of Patents and Trademarks*